(12) United States Patent
Dorfmueller et al.

(10) Patent No.: US 7,872,466 B2
(45) Date of Patent: Jan. 18, 2011

(54) RESISTIVE PARTICLE SENSORS HAVING MEASURING ELECTRODES

(75) Inventors: Lutz Dorfmueller, Gerlingen (DE); Ralf Schmidt, Gerlingen (DE); Markus Siebert, Leonberg (DE); Sabine Roesch, Ditzingen (DE); Helmut Marx, Hochdorf (DE); Henrik Schittenhelm, Stuttgart (DE); Gerd Teike, Hemmingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 10/582,546

(22) PCT Filed: Oct. 17, 2005

(86) PCT No.: PCT/EP2005/055307

§ 371 (c)(1),
(2), (4) Date: Apr. 11, 2007

(87) PCT Pub. No.: WO2006/061278

PCT Pub. Date: Jun. 15, 2006

(65) Prior Publication Data

US 2008/0024111 A1 Jan. 31, 2008

(30) Foreign Application Priority Data

Dec. 10, 2004 (DE) .................. 10 2004 059 650

(51) Int. Cl.
*G01N 27/00* (2006.01)
(52) U.S. Cl. ...................................... 324/71.4; 324/515
(58) Field of Classification Search ................ 324/71.4, 324/464
See application file for complete search history.

(56) References Cited

U.S. PATENT DOCUMENTS

| 4,307,061 | A | * | 12/1981 | Sarholz ....................... 422/94 |
| 4,571,543 | A | | 2/1986 | Raymond et al. |
| 4,916,384 | A | | 4/1990 | Ishida et al. |
| 5,858,192 | A | * | 1/1999 | Becker et al. ............... 204/547 |
| 6,634,210 | B1 | * | 10/2003 | Bosch et al. ............... 73/23.33 |
| 6,971,258 | B2 | * | 12/2005 | Rhodes et al. ............. 73/28.01 |
| 7,543,477 | B2 | * | 6/2009 | Berger et al. ............... 73/23.33 |
| 2005/0247559 | A1 | * | 11/2005 | Frey et al. .............. 204/403.01 |
| 2007/0158191 | A1 | * | 7/2007 | Berger ........................ 204/421 |

(Continued)

FOREIGN PATENT DOCUMENTS

DE 33 04 548 8/1984

(Continued)

OTHER PUBLICATIONS

Machine Translation WO 2004/097392, Nov. 11, 2004 PCT, Berger, German to English from freetranslation.com.*

*Primary Examiner*—Thomas Valone
(74) *Attorney, Agent, or Firm*—Kenyon & Kenyon LLP

(57) ABSTRACT

A sensor for determining the concentration of particles in gases, in particular of soot particles, has at least one substrate element, and a measuring area between at least one first and one second measuring electrode, the two measuring electrodes being configured so that by applying a voltage between the measuring electrodes, an asymmetric electric field is formed on the measuring area. The sides of the first and second measuring electrodes, facing one another, may not be parallel to one another, for example. Furthermore, at least one measuring electrode may have a structure along the side facing the other measuring electrode or along the finger electrodes.

6 Claims, 2 Drawing Sheets

U.S. PATENT DOCUMENTS

2007/0264158 A1* 11/2007 Schmidt et al. ............... 422/94
2008/0282769 A1* 11/2008 Nelson ...................... 73/23.31

FOREIGN PATENT DOCUMENTS

| | | |
|---|---|---|
| DE | 198 53 841 | 6/1999 |
| DE | 101 33 384 | 1/2003 |
| DE | 103 19 664 | 11/2004 |
| EP | 1 260 814 | 11/2002 |
| WO | WO 2004097392 | * 11/2004 |

* cited by examiner

RESISTIVE PARTICLE SENSORS HAVING MEASURING ELECTRODES

FIELD OF THE INVENTION

The present invention relates to a sensor for determining the concentration of particles in gases, in particular of soot particles.

BACKGROUND INFORMATION

Due to the environment-friendly efforts to reduce soot emissions of diesel engines, the need arises to determine the concentration of soot particles in the exhaust gas in a simple manner. In particular, monitoring the soot level downstream from a diesel particulate filter (DPF) during the operation of the vehicle is useful. In addition, it is necessary to predict the load of a diesel particulate filter for regeneration monitoring to achieve high system reliability.

To determine the soot concentration in the exhaust gas of internal combustion engines, a sensor having a device for detecting soot particles may be installed in the exhaust pipe.

German Patent documents nos. 101 33 384 A1 and 33 04 548 A1 discuss a resistive particle sensor, which has at least one non-conductive substrate element, measuring electrodes being situated on a substrate element. The measuring electrodes may be implemented in an interdigital comb structure. In an interdigital comb structure, each measuring electrode is formed by a series of individual finger electrodes, which are electrically connected to one another. The finger electrodes of both measuring electrodes alternatingly engage with one another, hence the designation "interdigital comb structure." Deposition of particles on the measuring surface between the electrodes, known as leakage current surface, results in a change in conductivity or impedance of the measuring surface between the fingers of the electrodes. For example, the resistance, the real part of the impedance, decreases with increasing particle concentration on the measuring surface. Alternatively, an increasing current at constant voltage applied between the measuring electrodes may be measured. The deposition, i.e., the deposition rate of particles, may be derived from the change in the particular measured quantity—the sensor signal.

This measuring method corresponds to an accumulating measuring principle, and the sooted sensor surfaces must therefore be freed of the conductive soot particles from time to time whenever a defined saturation current or another threshold value is attained. A high voltage to burn the soot particles via the current flow may be applied between the electrodes for regenerating the sooted surface. Alternatively, an integrated heater may heat the sensor affected by soot, so that the accumulated soot is fully burned off. After the soot particles have been burned off, the sensor is in its original state again, and a new measuring cycle including re-deposition and measurement of particles is thus made possible. Measuring and regeneration phases thus always alternate over time.

One disadvantage of this procedure is that no new deposition of particles is possible during the burn-off. Even after regeneration, soot cannot accumulate immediately; due to its thermal inertia, the sensor needs a certain time for the exhaust gas to bring the sensor element to its working temperature. Since no soot may accumulate during regeneration and the subsequent cooling phase of the sensor, the sensor is insensitive to any soot concentration present during these phases. Therefore, a measuring phase that is as long as possible is desirable. At the same time, the measured value must be large enough to enable early and meaningful determination of the particle concentration.

SUMMARY OF THE INVENTION

The sensor according to the exemplary embodiment and/or exemplary method of the present invention for determining the concentration of particles in gases, in particular of soot particles, has the advantage that the sensitivity of measurement is improved. In particular, the deposition rate of particles at constant particle concentration and thus the measured values also increase.

At the same time, the measuring phase is increased compared to the regeneration phase. Thus, using simple means, the sensor may be kept in the measuring phase for a longer time before the sensor signal shows saturation phenomena.

DETAILED DESCRIPTION

Figure 1A:
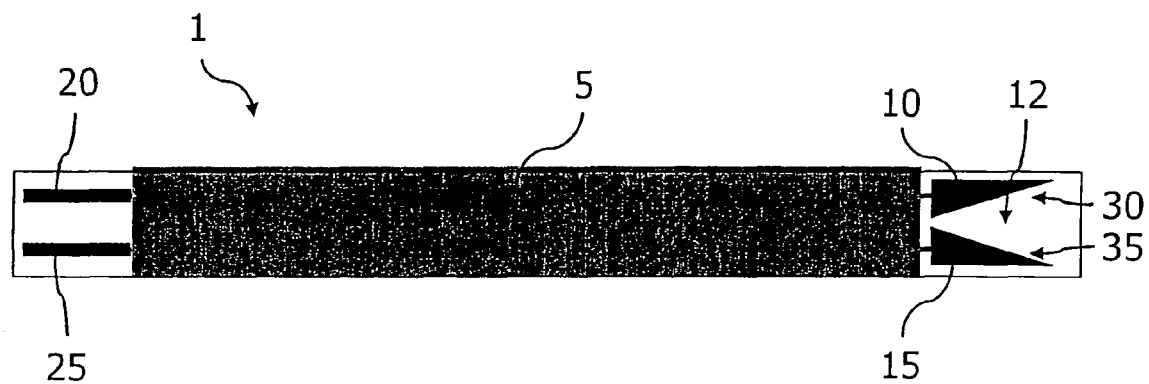
FIG. 1a shows an exemplary embodiment of a particle sensor having measuring electrodes situated on a substrate element, in top view.

In a first exemplary embodiment according to FIG. 1a, sensor 1 for determining the concentration of particles in gases, in particular of soot particles, has a substrate element 5, on which a first 10 and a second 15 measuring electrode are situated as a measuring device. The space between measuring electrodes 10, 15 is used as measuring area 12, on which the particles to be detected are deposited. The two measuring electrodes 10, 15 are connectable to a measuring and control unit (not shown in the figures) via contacts 20, 25 and a voltage may be applied to them. The measured value changes as a function of the state of particle deposition on measuring area 20. The measured value of resistance (impedance) or current intensity value measured via measuring electrodes 10, 15 is a function of the measuring mode.

As explained previously, the soot concentration in a gas may ultimately be determined from the measured values. The two measuring electrodes 10, 15 are configured according to the exemplary embodiment and/or exemplary method of the present invention in such a way that by applying a voltage between measuring electrodes 10, 15 an asymmetric electric field is formed on measuring area 12. A symmetric electric field is characterized in that the field has a constant direction and intensity all over the field. Such a field is formed, for example, by the interdigital comb electrodes known from the related art. The individual finger electrodes are typically implemented by unstructured, linear track conductors, which are all parallel to one another. This results in a constant electric field between the finger electrodes.

However, as FIG. 1 shows, in sensor 1, sides 30, 35 of first 10 and second 15 measuring electrodes, facing one another, are not parallel to one another. Instead, the distance between first 10 and second 15 measuring electrode decreases or increases continuously along the electrode. This creates an area having sides 30, 35 of measuring electrodes 10, 15, situated closely next to one another, and an area having sides 30, 35 of measuring electrodes 10, 15 situated wide apart. The transition from one area to the other is smooth and continuous. A non-constant field is created by applying a voltage. Particles that deposit on measuring area 12 of sensor 1 cause a reduction in resistance between measuring electrodes 10, 15 by forming conductive paths and thus create a sensor current.

A conductive path is first produced in the area of sides 30, 35 situated close to one another. Since the distance between measuring electrodes 10, 15 is very narrow at this point, a relatively slight particle deposition is sufficient for forming a conductive path and triggering a measuring signal. The sensitivity of sensor 1 is thus increased. As further particles deposit, conductive paths are also formed between sides 30, 35 of measuring electrodes 10, 15, which are farther apart. Due to the percolation characteristics of the deposited soot, whenever an additional conductive path is completed, a stronger increase in conductivity of the entire measuring area 12 takes place, which may be determined via measuring electrodes 10, 15. A stronger signal increase is thus achieved over a longer time period than would be possible in the case of measuring electrodes arranged in parallel. After short-circuiting measuring electrodes 10, 15 along all sides 30, 35, further deposits additionally keep increasing the conductivity continuously, i.e., measurement is also possible during this phase. Since the special configuration and arrangement of measuring electrodes 10, 15 allows a larger measuring area 12 to be formed for particle deposition, higher currents may also be achieved before they reach the saturation range compared to previously known interdigital measuring electrodes. The sensor signal is thus strengthened.

Figure 1B:
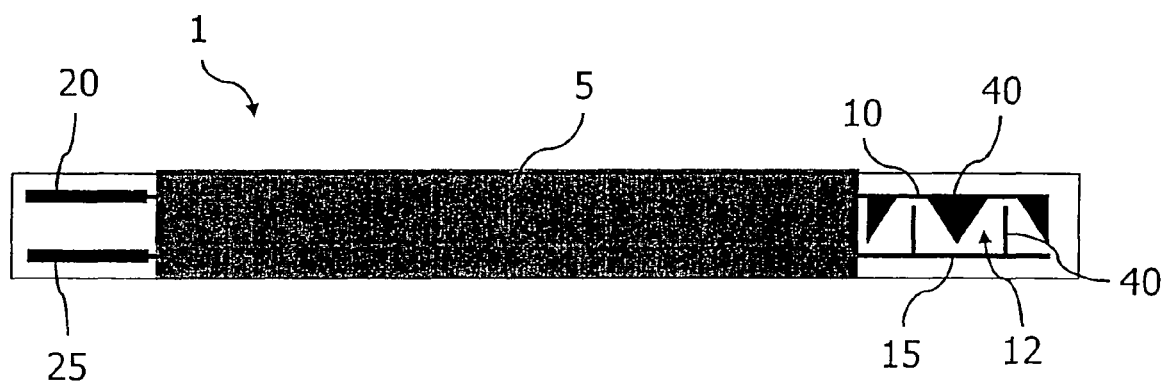
FIG. 1b shows another exemplary embodiment of a particle sensor having measuring electrodes situated on a substrate element, in top view.
Figure 2A:
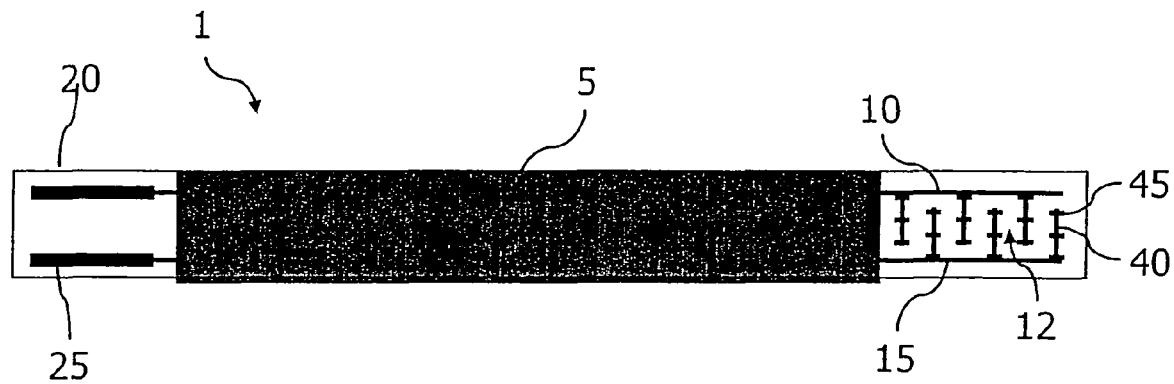
FIG. 2a shows another exemplary embodiment of a particle sensor having measuring electrodes situated on a substrate element, in top view.
Figure 2B:
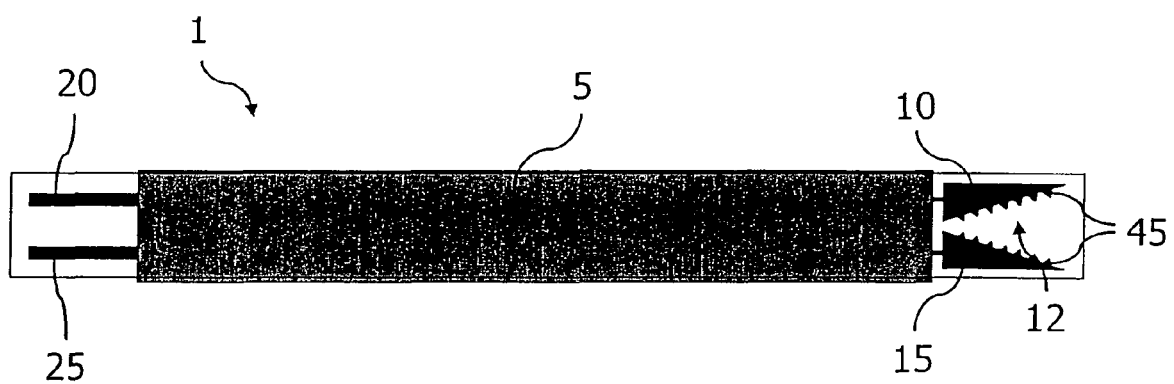
FIG. 2b shows another exemplary embodiment of a particle sensor having measuring electrodes situated on a substrate element, in top view.

A varying distance between the finger electrodes may also be achieved in a conventional interdigital comb structure by modifying its shape. As FIG. 1b shows, at least one measuring electrode 10, 15 may have finger electrodes 40 having varying widths. While in FIG. 1a, first and second measuring electrodes 10, 15 are triangular, in FIG. 2b individual finger electrodes 40 of a measuring electrode 10, 15 are triangular. The distance between two adjacent finger electrodes 40 thus changes continuously along the length of finger electrodes 40. This yields the same advantageous effects as described for the first embodiment. The pointed design also produces areas having a controlled direction of preferential growth of the deposited soot particles.

Figure 2C:
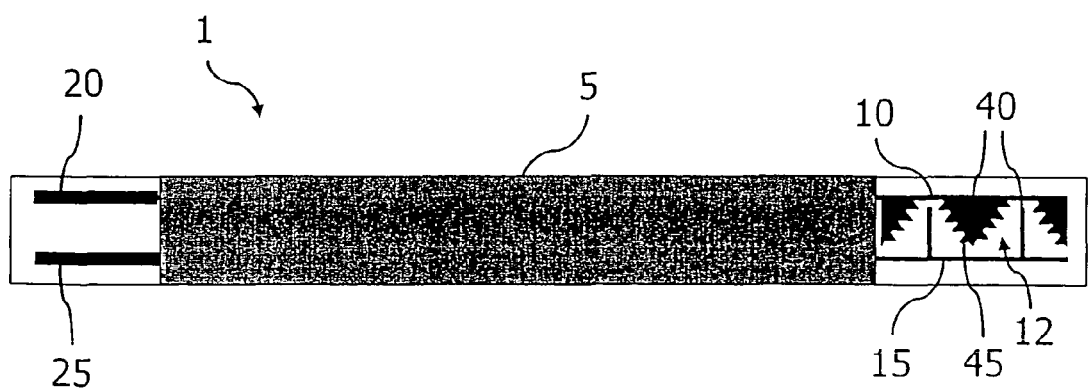
FIG. 2c shows another exemplary embodiment of a particle sensor having measuring electrodes situated on a substrate element, in top view.

All exemplary embodiments described so far have constantly smooth, unstructured sides of measuring electrodes 10, 15 or of individual finger electrodes 40. Alternatively (FIG. 2a) or additionally (FIGS. 2b, 2c), i.e., combined to form a varying distance between measuring electrodes 10, 15 or finger electrodes 40, it is proposed that at least one measuring electrode 10, 15 has a structure 45 along side 30, 35 facing the other measuring electrode 15, 10 or along finger electrodes 40. Structure 45 is formed by regularly arranged tips, squares, dots, or other geometric shapes. Such structures 45 on the electrode sides result in increased field step-up when a voltage is applied. Structured finger electrodes 40, as in FIG. 2a, alone result in a non-constant electric field on measuring area 12. This increase in field step-up causes polarizable or already charged particles to deposit preferentially compared to electrodes without structured sides for the same voltage applied. The particle deposition rate thus increases due to the increased field gradients. Consequently, higher sensor currents are achieved for a given particle concentration. This may make the use of simplified measuring electronics in the control unit for signal analysis possible, since leakage currents or EMC (electromagnetic compatibility) currents have only a slight interfering effect.

Summarizing, measuring electrodes 10, 15 are configured in all embodiments in such a way that by applying a voltage between measuring electrodes 10, 15 an asymmetric electric field is formed on measuring area 12. The asymmetric electric field is an electric field that is non-homogeneous in space. The special design of the field distribution makes targeted particle deposition control in space possible. In particular, the formation of conductive paths in preferred areas may be controlled. Path growth over time may also be steered in a desired direction. If necessary, more than two measuring electrodes 10, 15 may be provided for this purpose, for example, at least one central electrode (not shown in the figures) may be additionally provided between first and second measuring electrodes 10, 15. The geometric shape of and the potential applied to all electrodes is to be adapted to the desired field distribution.

What is claimed is:

1. A sensor for determining a concentration of particles in gases, comprising:
   at least one substrate element;
   a first measuring electrode; and
   a second measuring electrode, wherein there is a measuring area between the first measuring electrode and the second measuring electrode, wherein the first and second measuring electrodes are arranged so that by applying a voltage between the measuring electrodes an asymmetric electric field is formed on the measuring area; wherein the first and second measuring electrodes each include finger electrodes that are interdigitated to form an interdigital comb structure, and wherein the finger electrodes of at least one of the measuring electrodes have varying widths;
   wherein the finger electrodes of at least one measuring electrode have regularly arranged geometrically shaped structures along sides of the finger electrodes facing adjacent finger electrodes of the other measuring electrode.

2. The sensor of claim 1, wherein sides of the first and second measuring electrodes, facing one another, are not parallel to one another.

3. The sensor of claim 1, wherein a distance between the first and second measuring electrodes one of increases and decreases continuously along the electrodes.

4. The sensor of claim 1, wherein the regularly arranged geometric shapes include at least one of tips, squares and dots.

5. The sensor of claim 1, wherein at least one central electrode is provided between the first measuring electrode and the second measuring electrode.

6. The sensor of claim 1, wherein the particles include soot particles.

* * * * *